(12) United States Patent
Kampouris et al.

(10) Patent No.: US 8,877,038 B2
(45) Date of Patent: Nov. 4, 2014

(54) ELECTROCHEMICAL ASSAY

(75) Inventors: Dimitrios Konstantinos Kampouris, Nottingham (GB); Rashid Olukayoee Kadara, Nottingham (GB); Patrick Robinson Huddleston, Nottingham (GB); Craig Edward Banks, Nottingham (GB)

(73) Assignee: Oxtox Limited, Stockport (GB)

( * ) Notice: Subject to any disclaimer, the term of this patent is extended or adjusted under 35 U.S.C. 154(b) by 372 days.

(21) Appl. No.: 12/989,412

(22) PCT Filed: Apr. 24, 2009

(86) PCT No.: PCT/GB2009/001047
§ 371 (c)(1),
(2), (4) Date: Dec. 22, 2010

(87) PCT Pub. No.: WO2009/130471
PCT Pub. Date: Oct. 29, 2009

(65) Prior Publication Data
US 2011/0168576 A1 Jul. 14, 2011

(30) Foreign Application Priority Data

Apr. 24, 2008 (GB) .................................. 0807534.3

(51) Int. Cl.
*G01N 27/327* (2006.01)
*G01N 33/487* (2006.01)
*G01N 27/30* (2006.01)

(52) U.S. Cl.
CPC ........ *G01N 33/48714* (2013.01); *G01N 27/302* (2013.01)
USPC .......................... 205/792; 205/787; 204/403.1

(58) Field of Classification Search
USPC ............. 204/403.01–403.15; 205/787, 777.5, 205/778, 792, 789, 789.5
See application file for complete search history.

(56) References Cited

U.S. PATENT DOCUMENTS

| | | | | |
|---|---|---|---|---|
| 4,524,217 A | * | 6/1985 | Davenport et al. | 564/223 |
| 5,113,018 A | * | 5/1992 | Kurano et al. | 564/403 |
| 5,332,479 A | * | 7/1994 | Uenoyama et al. | 205/777.5 |

FOREIGN PATENT DOCUMENTS

| | | |
|---|---|---|
| EP | 0402935 | 12/1990 |
| WO | WO2006/134386 | 12/2006 |

(Continued)

OTHER PUBLICATIONS

Josephy et al. "Reaction of Gibbs Reagent with Para-Substituted Phenols," Anal. Chem. 1984, 56, 813-814.*

(Continued)

*Primary Examiner* — Alex Noguerola
(74) *Attorney, Agent, or Firm* — Iphorgan Ltd.

(57) ABSTRACT

The invention provides an electrochemical assay for a phenol analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding to said phenol analyte, characterized in that said first compound in its oxidized or reduced form comprises a group of structure I R1-NH—C*—(C*—C*)$_n$—C*-QR' (I) (where n is 0 or 1; Q is O, S, NH or NR'; C*—(C*—C*)$_n$—C* is a two or four carbon string in a conjugated delocalised electron system optionally substituted by a group comprising R; R is an electron-donating or withdrawing substituent; and R' is H or a group R, at least one group R' being a group R).

18 Claims, 1 Drawing Sheet

(56) References Cited

FOREIGN PATENT DOCUMENTS

WO    WO 2006134386 A1 * 12/2006
WO    2008/003999    1/2008

OTHER PUBLICATIONS

DeRiemer et al., "Synthesis of Mono- and Dinucleotide Photoaffinity Probes of Ribonucleic Acid Polymerase," Biochemistry 1981, 20, 1606-1612.*

Adam et al., "Adsorption of Phenolics from Aqueous Solution on Activated Carbon: Effect of Molecular Structure", Journal of Al-Nahrain University, vol. 10(2), Dec. 2007, pp. 7-12.*

Goyal R. N. et al; "Voltammetric determination of paracetamol at C60-modified glassy carbon electrode"; Electrochimica Acta, Elsevier Science Publishers, Barking, GB, vol. 51, No. 15, Apr. 1, 2006, pp. 3008-3012, Experimental Abstract.

Eleanor R. Lowe et al; "Indirect detection of substitued phenols and cannabis based on the electochemical adaptation of the Gibbs reaction"; Analytical and Bioannalytical Chemistry, Springer, Berlin, DE, vol. 383, No. 3, Oct. 1, 2005, pp. 523-531.

Goodwin Alexander et al; "Graphite micropowder modified with 4-amino-2, 6-diphenylphenol supported on basal plane pyrolytic graphite electrodes; Micro sensing platforms for the indirect electrochemical detection of Delta (9)-tetrahydrocannabinol in saliva" Electroanalysis, vol. 18, No. 11, Jun. 2006, pp. 1063-1067.

International Search Report and Written Opinion; PCT/GB2009/001047; European Patent Office acting as the International Search Authority, dated Nov. 16, 2009.

Alexander Goodwin et al., "Tagging of Model Amphetamines with Sodium 1,2-Naphthoquinone-4-sulfonate: Application to the Indirect Electrochemical Detection of Amphetamines in Oral (Saliva) Fluid" Electroanalysis 18.

Josephy et al., "Reaction of Gibbs Reagent with Para-Substituted Phenols" Analytical Chemistry 56(4):813-814 (1984).

European Patent Office, Examination Report issued May 27, 2014 in European Application No. 09 734 817.1-1554, completed from PCT Application No. PCT/GB09/001047.

* cited by examiner

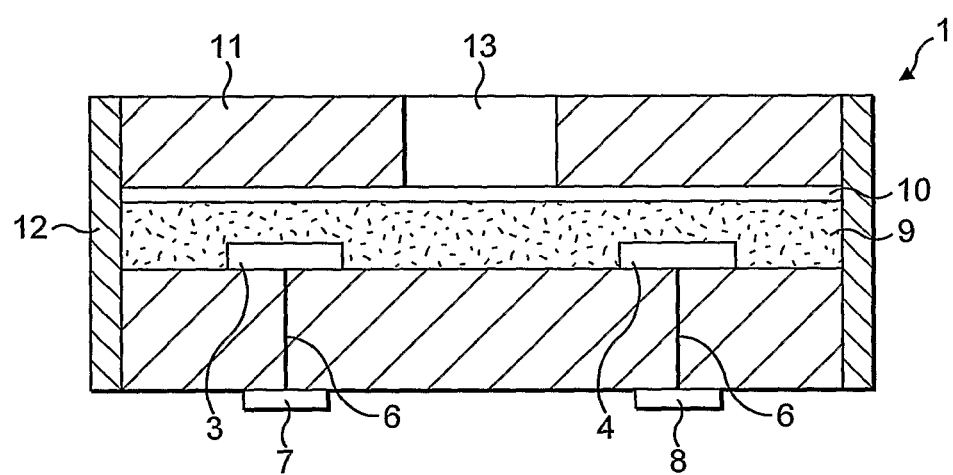

ELECTROCHEMICAL ASSAY

This invention relates to improvements in and relating to assay methods and assay devices, in particular methods and devices for testing electrochemically for the presence of drug substances or their metabolites in body fluids, in particular oral fluids such as saliva.

In many circumstances it is desirable to test an individual for consumption of or exposure to a drug substance, in particular substances which affect physical performance or whose use is illegal. Examples include opiates, cannabis, amphetamines, steroids, and alcohol. Since the person being tested may be innocent of drug consumption, since testing may be frequently repeated, and since many individuals may be tested, it is desirable that such tests are non-invasive, rapid, sufficiently accurate, and inexpensive. Where testing is to be of members of the general public, it is also particularly desirable that testing should not be undignified.

For this latter reason, it is desirable that the body tissue or fluid sample to be tested should be obtainable rapidly, without pain and without loss of dignity to the subject being tested.

Drug substances and their metabolites may be found in many body tissues or fluids, typically blood, saliva, sweat, breath, urine, faeces, hair, mucus, semen and vaginal fluid. For non-invasive, large scale testing, saliva, sweat, inner mouth surface mucus, and hair perhaps represent the materials of which samples can be taken with least objection by the test subject.

Traditional test methods for determining the presence of drug substances or their metabolites in such samples have frequently employed antibodies capable of binding to the analyte and systems for detecting the resulting antibody:analyte conjugates. Antibody-based methods however are generally relatively expensive, require multiple assay steps, and can be time consuming, as compared to the cheap and rapid breathalyzer tests routinely used by police for roadside testing of drivers suspected to have consumed excessive alcohol.

We have recently developed electrochemical tests for cannabis and amphetamines or their metabolites in the saliva of test subjects that do meet the requirements set out above for rapidity, dignity and low expense. These are described for example in WO2006/134386, WO2008/003999 and in Goodwin et al Electroanalysis 18: 1833-1837 (2006), the contents of which are hereby incorporated by reference.

These electrochemical tests involve placing a redox compound (i.e. one capable of reversibly converting between an oxidized form and a reduced form) adjacent to a working electrode, placing the saliva sample between the working electrode and a counter-electrode, applying a time varying voltage across the electrodes, and detecting the resultant current. In these tests, besides the working- and counter-electrodes, a reference electrode is generally also used. In a preferred embodiment, the applied voltage alternates in direction and the technique is referred to as cyclic voltammetry. However, a stepped voltage may instead be used in which case the technique is referred to as chronoamperometry. Likewise, square-wave and differential pulse voltammetry may be used.

The redox compound used in these tests is one which, in one redox state but not the other, could bind essentially irreversibly to the analyte compound thereby reducing the maximum current as the voltage is alternated. This technique is known as cyclic voltammetry.

While our technique works well, it is desirable that its performance and accuracy be improved and the present invention relates in particular to such improvements.

As with many analytical techniques where the test sample is a complex mixture of substances, other test sample components may contribute to the detected signal, i.e. by providing 'noise' or interference.

We have found that such noise or interference in the test for cannabis and its metabolites may result from the sensitivity of the redox compound and that this may be reduced or enhanced as desired by selected substitution of an amine group or carbon string in the redox compound, i.e. substitution with groups that are more or less electron-withdrawing than the hydrogen they replace—more and less electron-withdrawing substituents serving respectively to increase or decrease the sensitivity of the redox compound.

Viewed from this aspect the invention provides an electrochemical assay for a phenol analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding (e.g. covalently bonding) to said phenol analyte, characterized in that said first compound in its oxidized or reduced form comprises a group of structure I

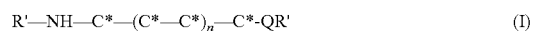

(where n is 0 or 1, preferably 1; Q is O, S, NH or NR'; C*—(C*—C*)$_n$—C* is a two or four carbon string in a conjugated delocalised electron system (e.g. an aromatic ring, for example a benzene or fused benzene ring) optionally substituted by a group comprising R; R is an electron-donating or withdrawing substituent; and R' is H or a group R, at least one group R' being a group R).

At least some of these compounds comprising groups of structure I are themselves novel and form a further aspect of the invention. Viewed from this aspect the invention provides a compound capable of reversible oxidation and reduction and in either an oxidized or a reduced form of binding (e.g. covalently bonding) to a phenol, characterized in that in its oxidized or reduced form it comprises a group of structure I

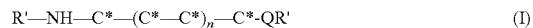

(where n is 0 or 1, preferably 1; Q is O, S, NH or NR'; C*—(C*—C*)$_n$—C* is a two or four carbon string in a conjugated delocalised electron system (e.g. an aromatic ring, for example a benzene or fused benzene ring) optionally substituted by a group comprising R; R is an electron-donating or withdrawing substituent; and R' is H or a group R, at least one group R' being a group R).

Viewed from a further aspect the invention provides an electrode assembly for use in an assay according to the invention comprising a working electrode, a counter-electrode, a liquid sample-receiving zone which when a liquid sample is applied thereto allows electrical contact of said sample (or fluid therefrom) with said electrodes, and a first compound capable of reversible oxidation and reduction disposed at said working electrode, said first compound being capable in either an oxidized or a reduced form of binding (e.g. covalently bonding) to a phenol analyte, characterized in that said first compound in its oxidized or reduced form comprises a group of structure I

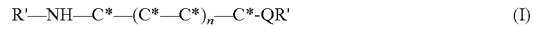

(where n is 0 or 1, preferably 1; Q is O, S, NH or NR'; C*—(C*—C*)$_n$—C* is a two or four carbon string in a conjugated delocalised electron system (e.g. an aromatic ring, for example a benzene or fused benzene ring) optionally substituted by a group comprising R; R is an electron-donating or withdrawing substituent; and R' is H or a group R, at least one group R' being a group R).

In these first compounds, a group R in the functional group NHR' serves to modify the reactivity of the first compound to the phenol analyte. Electron withdrawing R groups increase activity and electron donating groups, which are preferred, serve to reduce activity. Electron-withdrawing or donating is of course judged relative to hydrogen. Examples of typical groups R include halogen (e.g. Cl), acyl (e.g. $CH_3CO$), aryl (e.g. phenyl), alkyl, alkenyl, aralkyl, etc. Preferably any R group contains up to 20 carbons, especially up to 12 carbon atoms and optionally is substituted with a functional group by which it may be bound, covalently or non-covalently, to a substrate, e.g. thiol, hydroxyl, carboxyl, vinyl, or diazonium groups. Such functional groups, while preferably present in a group NHR' in structure I may additionally or alternatively be present as or on substituents at the remaining skeletal positions of the first compound, e.g. the carbons of the $C^*_2$ or $C^*_4$ chain.

The groups R may be introduced onto the otherwise unsubstituted first compound by conventional chemical reactions, optionally preceded by protection of groups where R substitution is undesired and followed by cleavage of the protecting groups. Thus for example an acetyl group may be introduced by reaction of the primary amine with acetyl chloride.

As mentioned above, the group of structure I in the first compound is preferably part of an aromatic ring, particularly a benzene ring.

Examples of suitable substituents on the carbons of the aromatic ring are given in WO2006/134386. As indicated above, such substituents may include functional groups for attachment to a substrate as mentioned above.

Preferred first compounds thus include optionally substituted 1-(substituted-amino)-4-amino benzenes, 1-(substituted-amino)-4-hydroxy-benzenes, 1-(substituted-amino)-2-amino-benzenes, 1-(substituted-amino)-2-hydroxy-benzenes, 1,4-di(substituted-amino)-benzenes, and 1,2-di(substituted-amino)-benzenes.

We have also found that such noise or interference may be significantly reduced if a semi-permeable membrane is interposed between the working electrode and the saliva sample.

Thus viewed from one aspect the invention provides an electrochemical assay for a drug substance analyte in a saliva sample wherein an oral fluid (e.g. saliva) sample is interposed between a working electrode and a counter-electrode, and wherein a first compound capable of reversible oxidation and reduction is disposed at said working electrode, said first compound being capable in either an oxidized or a reduced form of binding to said analyte, characterized in that a semi-permeable membrane is disposed to prevent direct contact between the saliva sample as applied and at least said working electrode.

Viewed from a further aspect the invention provides an electrode assembly for use in an assay according to the invention comprising a working electrode, a counter-electrode, a liquid sample-receiving zone which when a liquid sample is applied thereto allows electrical contact of said sample (or fluid therefrom) with said electrodes, and a semi-permeable membrane disposed between said sample-receiving zone and at least said working electrode.

This assay format is especially preferred for use in detection of opiates and alkaloids, e.g. heroin and cocaine, where no reaction between analyte and redox compound is required where a working electrode is used which comprises edge plane pyrolytic graphite (eppg).

Thus viewed from a further aspect the invention provides an electrochemical assay for an opiate or alkaloid analyte in a body fluid sample, wherein said sample is interposed between a working electrode and a counter-electrode, characterized in that a semi-permeable membrane is disposed to prevent direct contact between the saliva sample as applied and at least said working electrode and in that said working electrode comprises a carbon material selected from edge plane pyrolytic graphite and carbon nanotubes or nanofibres.

The edge plane pyrolytic graphite may be provided for example by regular graphite, by graphite having at least a few percent more eppg than regular graphite, by graphite having at least about 50% eppg (e.g. spherical graphite), or by a single aligned crystal in which substantially all the sites are eppg. Preferably eppg contributes at least 50%, more preferably at least 60%, e.g. at least 75%, especially at least 90% of the graphite surface.

The edge plane sites/defects in eppg provide optimal electrode kinetics and the percentage of edge plane sites/defects to basal plane sites/defects can be tailored to move the voltammetric peak to the desired potential. This allows separation of the analyte peaks from those of possible interfering compounds.

Eppg may be produced from highly ordered pyrolytic graphite and is available commercially from the SPI Supplies Division of Structure Probe Inc., PA, USA.

Carbon nanofibres may be prepared by transformation of a carbonaceous gas, e.g. methane or carbon monoxide, on porous metal particles, e.g. porous nickel particles. Carbon nanotubes, both single and multi-walled are well known from the scientific literature.

In these assays, the semi-permeable membrane preferably comprises both anionic and cationic groups to screen out both cationic and anionic species from penetrating to the working electrode.

The semi-permeable membrane may for example be cellulose acetate or a conventional dialysis membrane. Other suitable membrane materials include nafion, polyvinylsulphonate, carboxymethylcellulose, diethylaminoethylcellulose, polylysine and sulphonated polymers such as the sulphonated polyester available as AQ55 from Eastman Chemical Co., TN, USA.

The ionic strength of oral fluids such as saliva can be highly variable and the membrane advantageously includes a polyelectrolyte to increase the ionic strength near the surface of the working electrode. One example of a suitable material for use in this regard is poly(diethyldiallylammonium chloride). The membrane moreover may be provided with a hydrophilic or hydrophobic sample contact surface as desired. In this regard, polymers such as polysiloxanes or polyvinylpyrrolidone may be used. Thus for example a microperforated hydrophobic polymer overlying a hydrophilic polymer layer may be suitable for tongue contact.

The use of the semi-permeable membrane is also especially preferred when the analyte is an amphetamine or a metabolite thereof. For such assays, the redox compound is preferably a 1,2-dione as described in WO2008/03999, an equivalent 1,4-conjugated dione, or an analog thereof functionally modified for bonding to the working electrode as described later herein.

We have also found that the results of cyclic voltametric testing for analytes in this fashion are sensitive to time and that consistency of results may be improved by binding the redox compound (e.g. the "first compound") to the electrode material rather than simply coating it onto or mixing it with the electrode material. This reduces leaching of the redox compound away from the working electrode and has the added advantages that the redox compound may be used more efficiently and that no toxicity problems will arise with the bound redox compounds. This again means that direct oral contract with the working electrode becomes feasible, so simplifying the design of suitable assay kits.

Thus viewed from a further aspect the invention provides an electrochemical assay for an analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding (e.g. covalently bonding) to said analyte, characterized in that said first compound is chemically bound to said working electrode.

Viewed from a further aspect the invention provides an electrode assembly for use in an assay according to the invention comprising a working electrode, a counter-electrode, a liquid sample-receiving zone which when a liquid sample is applied thereto allows electrical contact of said sample (or fluid therefrom) with said electrodes, and a first compound capable of reversible oxidation and reduction disposed at said working electrode, said first compound being capable in either an oxidized or a reduced form of binding (e.g. covalently bonding) to an analyte, characterized in that said first compound is chemically bound to said working electrode.

Thus, for example, carbon electrodes can be reacted with redox compounds functionalized with diazonium groups or gold electrodes may be reacted with redox compounds carrying pendent thiol groups, or redox compounds carrying nitro groups may be reacted electrochemically to bind with carbon electrodes, or redox compounds with pendent unsaturated carbon bonds (e.g. vinyl groups) may on polymerization bind to carbon electrodes, and so forth.

Once again, these functional groups may be introduced onto the redox compound using standard synthetic chemistry techniques.

The working electrode to which the redox compound is bound in this way may be in any convenient form, e.g. sheet, fiber, compacted particulate mixture, etc., and may be deposited, e.g. coated or printed onto, an electrode support. The use of printed or compacted particulate material, e.g. nanometer to micrometer sized metal or carbon particles, is especially preferred for ease of construction of the assay equipment.

In order further to increase the accuracy of the electrochemical assays, it is preferred to associate with the working electrode a further redox compound which does not in either redox state bind (e.g. covalently bond) to the analyte. In this way the signal from the second redox compound may be used to normalize that from the first redox compound which does react with the analyte. The further redox compound may also be substituted with electron withdrawing or donating groups to shift its redox response to the desired potential region.

Thus in a preferred embodiment of the invention in the electrochemical assay for an analyte in a body fluid sample the said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first and a second compound each capable of reversible oxidation and reduction is disposed at said working electrode, said first compound being capable in either an oxidized or a reduced form of binding (e.g. covalently bonding) to said analyte and said second compound not being capable in either oxidized or reduced form of binding (e.g. covalently bonding) to said analyte, and wherein the component of the variation in current between said working and counter-electrodes corresponding to oxidation or reduction of said second compound is used to normalize the component of the variation in current between said working and counter-electrodes corresponding to oxidation or reduction of said first compound.

Likewise in a preferred embodiment of the electrode assembly for use in an assay according to the invention, the assembly comprises a working electrode, a counter-electrode, a liquid sample-receiving zone which when a liquid sample is applied thereto allows electrical contact of said sample (or fluid therefrom) with said electrodes, and a first and a second compound each capable of reversible oxidation and reduction is disposed at said working electrode, said first compound being capable in either an oxidized or a reduced form of binding (e.g. covalently bonding) to an analyte, and said second compound not being capable in either oxidized or reduced form of binding (e.g. covalently bonding) to said analyte.

Where the first redox compound is chemically bound to the working electrode, the second redox compound is desirably likewise bound and where said first redox compound is unbound, the second redox compound is desirably likewise unbound.

The second redox compound will generally be selected so as to avoid overlap of its signal with that of the first redox compound. Thus, for example, where an amino compound is used as the first redox compound in the detection of a phenol analyte, e.g. a cannabis metabolite, it may be convenient to use an anthraquinone as the second redox compound, while for detection of amphetamines using a naphthoquinone as the first redox compound it may be convenient to use ferrocene compounds (e.g. decamethylferrocene or poly(vinylferrocene)) as the second redox compound, etc. To ensure the redox signals for the two redox compounds are appropriately spaced apart, they may be substituted by electron withdrawing or donating groups as required. Other suitable second redox compounds include anthracenes, e.g. vinylanthracene.

Viewed from a further aspect the invention provides an assay device comprising a voltage source, a current meter and a detachable electrode assembly according to the invention.

It will be appreciated that a single assay may combine two or more of the assays of the invention where the features thereof are not incompatible.

The invention will now be described in further detail with reference to the following non-limiting Examples and the accompanying drawings, in which FIG. 1 is a schematic cross-sectional view of an electrode assembly according to the invention having a semi-permeable membrane.

Referring to FIG. 1, there is shown an electrode assembly 1 in the form of an assay cartridge for insertion into an assay reader.

The assembly comprises an impervious base plate 2 carrying a working electrode 3 and a counter-electrode 4 connected by electrical leads 5 and 6 to electrical connections 7 and 8. Above base plate 2 are disposed a porous web 9, a semi-permeable membrane 10 and an apertured impervious cover plate 11. The various layers are held together by impervious casing 12. In use, a liquid body sample, preferably saliva, is placed in aperture 13 in cover plate 11 and allowed to diffuse through membrane 10 to permeate web 9. The assembly is then placed in a reader, not shown, which connects connections 7 and 8 to a cycled voltage source and a current meter.

EXAMPLE 1

Preparation of Redox Compounds

Acetylation of 1,4-Phenylenediamine with Acetic Anhydride

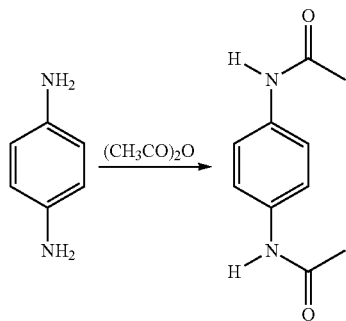

EXAMPLE 2

Preparation of Redox Electrode-Bound Compounds

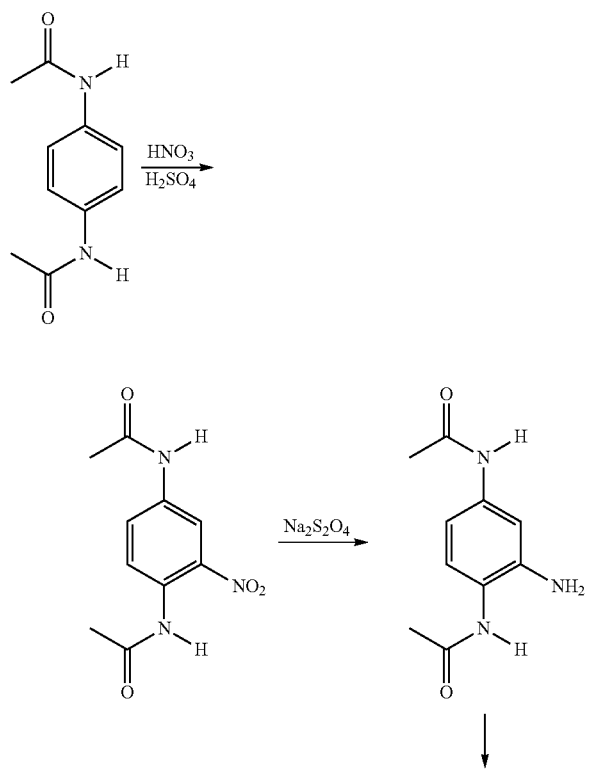

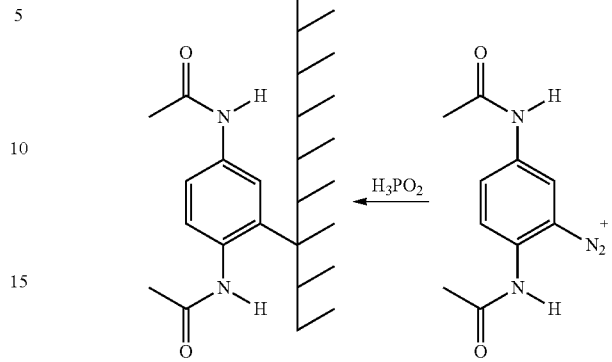

The invention claimed is:

1. An electrochemical assay for a phenol analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding to said phenol analyte, wherein said first compound in its oxidized or reduced form comprises a group of structure I $$R'-NH-C^*-(C^*-C^*)_n-C^*-OR' \qquad (I)$$

where n is 0 or 1; Q is O, S, NH or NR';
$C^*-(C^*-C^*)_n-C^*$ is a two or four carbon string in a conjugated delocalised electron system substituted by 0 or 1 group comprising R;
R is an electron-donating or withdrawing substituent; and
R' is H or a group R, at least one group R' being a group R.

2. The assay as claimed in claim 1 further comprising a second compound capable of reversible oxidation and reduction disposed at said working electrode, said first compound being capable in either an oxidized or a reduced form of binding to said analyte and said second compound not being capable in either oxidized or reduced form of binding to said analyte, and wherein the component of the variation in current between said working and counter-electrodes corresponding to oxidation or reduction of said second compound is used to normalize the component of the variation in current between said working and counter-electrodes corresponding to oxidation or reduction of said first compound.

3. The assay as claimed in either of claims 1 or 2, said first compound being capable in either an oxidized or a reduced form of binding to said analyte, wherein said first compound is chemically bound to said working electrode.

4. The assay as claimed in claim 3, wherein said phenol analyte is a drug substance analyte and said body fluid sample is a saliva sample, wherein said saliva sample is interposed between a working electrode and a counter-electrode and further comprising a semi-permeable membrane disposed to prevent direct contact between the saliva sample as applied and at least said working electrode.

5. The assay as claimed in either of claims 1 or 2, wherein said phenol analyte is a drug substance analyte and wherein said body fluid sample is a saliva sample, and wherein said saliva sample is interposed between said working electrode and said counter-electrode, and further comprising a semi-permeable membrane disposed to prevent direct contact between the saliva sample as applied and at least said working electrode.

6. An electrode assembly for use in an assay according to either of claims 1 or 2 comprising a working electrode, a counter-electrode, a liquid sample-receiving zone which when a liquid sample is applied thereto allows electrical contact of said sample or fluid therefrom with said electrodes, and a first compound capable of reversible oxidation and reduction disposed at said working electrode, said first compound being capable in either an oxidized or a reduced form of binding to a phenol analyte, wherein said first compound in its oxidized or reduced form comprises a group of structure I

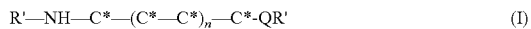

$$R'-NH-C^*-(C^*-C^*)_n-C^*-QR' \quad (I)$$

where n is 0 or 1; Q is O, S, NH or NR'; $C^*-(C^*-C^*)_n-C^*$ is a two or four carbon string in a conjugated delocalised electron system substituted by 0 or 1 group comprising R;

R is an electron-donating or withdrawing substituent; and R' is H or a group R, at least one group R' being a group R.

7. The electrode assembly as claimed in claim 6, further comprising a second compound capable of reversible oxidation and reduction disposed at said working electrode, said first compound being capable in either an oxidized or a reduced form of binding to an analyte, and said second compound not being capable in either oxidized or reduced form of binding to said analyte.

8. The electrode assembly as claimed in claim 7 further comprising a semi-permeable membrane disposed between said sample-receiving zone and at least said working electrode.

9. The electrode assembly as claimed in claim 7, wherein said first compound is chemically bound to said working electrode.

10. The electrode assembly as claimed in claim 6 further comprising a semi-permeable membrane disposed between said sample-receiving zone and at least said working electrode.

11. The electrode assembly as claimed in claim 10, wherein said first compound is chemically bound to said working electrode.

12. The electrode assembly as claimed in claim 6, said first compound being capable in either an oxidized or a reduced form of binding to an analyte, wherein said first compound is chemically bound to said working electrode.

13. An assay device comprising a voltage source, a current meter and a detachable electrode assembly according to claim 6.

14. The device of claim 13, wherein the electrode assembly comprises a working electrode, a counter-electrode, a liquid sample-receiving zone which when a liquid sample is applied thereto allows electrical contact of said sample or fluid therefrom with said electrodes, and a first compound capable of reversible oxidation and reduction disposed at said working electrode, said first compound being capable in either an oxidized or a reduced form of binding to a phenol analyte, wherein said first compound in its oxidized or reduced form comprises a group of structure I

$$R'-NH-C^*-(C^*-C^*)_n-C^*-QR' \quad (I)$$

where n is 0 or 1; Q is O, S, NH or NR'; $C^*-(C^*-C^*)_n-C^*$ is a two or four carbon string in a conjugated delocalised electron system optionally substituted by a group comprising R;

R is an electron-donating or withdrawing substituent; and R' is H or a group R, at least one group R' being a group R'; and further comprising a second compound capable of reversible oxidation and reduction disposed at said working electrode, said first compound being capable in either an oxidized or a reduced form of binding to an analyte, and said second compound not being capable in either oxidized or reduced form of binding to said analyte.

15. The device of claim 13, wherein the electrode assembly comprises a working electrode, a counter-electrode, a liquid sample-receiving zone which when a liquid sample is applied thereto allows electrical contact of said sample or fluid therefrom with said electrodes, and a first compound capable of reversible oxidation and reduction disposed at said working electrode, said first compound being capable in either an oxidized or a reduced form of binding to a phenol analyte, wherein said first compound in its oxidized or reduced form comprises a group of structure I

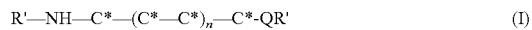

$$R'-NH-C^*-(C^*-C^*)_n-C^*-QR' \quad (I)$$

where n is 0 or 1; Q is O, S, NH or NR'; $C^*-(C^*-C^*)_n-C^*$ is a two or four carbon string in a conjugated delocalised electron system optionally substituted by a group comprising R;

R is an electron-donating or withdrawing substituent; and R' is H or a group R, at least one group R' being a group R'; and further comprises a semi-permeable membrane disposed between said sample-receiving zone at least said working electrode.

16. The device of claim 13, wherein the electrode assembly comprises a working electrode, a counter-electrode, a liquid sample-receiving zone which when a liquid sample is applied thereto allows electrical contact of said sample or fluid therefrom with said electrodes, and a first compound capable of reversible oxidation and reduction disposed at said working electrode, said first compound being capable in either an oxidized or a reduced form of binding to a phenol analyte, wherein said first compound in its oxidized or reduced form comprises a group of structure I

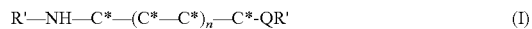

$$R'-NH-C^*-(C^*-C^*)_n-C^*-QR' \quad (I)$$

where n is 0 or 1; Q is O, S, NH or NR'; $C^*-(C^*-C^*)_n-C^*$ is a two or four carbon string in a conjugated delocalised electron system optionally substituted by a group comprising R;

R is an electron-donating or withdrawing substituent; and R' is H or a group R, at least one group R' being a group R'; and wherein said first compound is chemically bound to said working electrode.

17. The electrode assembly of claim 6 for use in an electrochemical assay for a phenol analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding to said phenol analyte, wherein said first compound in its oxidized or reduced form comprises a group of structure I

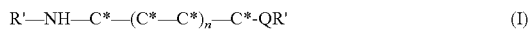   (I)

where n is 0 or 1; Q is O, S, NH or NR';
C*—(C*—C*)$_n$—C* is a two or four carbon string in a conjugated delocalised electron system substituted by 0 or 1 group comprising R;
R is an electron-donating or withdrawing substituent; and
R' is H or a group R, at least one group R' being a group R;
and wherein said first compound is chemically bound to said working electrode.

18. The electrode assembly of claim 6 for use in an electrochemical assay for a phenol analyte in a body fluid sample wherein said sample, or fluid therefrom, is contacted with the working electrode of an electrode assembly comprising a working electrode, a counter-electrode, a voltage supply to said working and counter-electrodes and a current meter for determining the current between said working and counter-electrodes, and wherein a first compound capable of reversible oxidation and reduction is disposed at said working electrode, said first compound being capable in either an oxidized or a reduced form of binding to said phenol analyte, wherein said first compound in its oxidized or reduced form comprises a group of structure I

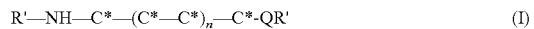   (I)

where n is 0 or 1; Q is O, S, NH or NR';
C*—(C*—C*)$_n$—C* is a two or four carbon string in a conjugated delocalised electron system substituted by 0 or 1 group comprising R;
R is an electron-donating or withdrawing substituent; and
R' is H or a group R, at least one group R' being a group R;
wherein said body fluid sample is a saliva sample and the phenol analyte is a drug substance analyte; and
wherein an oral fluid sample is interposed between the working electrode and the counter-electrode; and
further comprising a semi-permeable membrane disposed to prevent direct contact between the saliva sample as applied and at least said working electrode.

* * * * *